United States Patent
Servidio et al.

(10) Patent No.: US 11,678,992 B2
(45) Date of Patent: Jun. 20, 2023

(54) VARIABLE THICKNESS FEMORAL AUGMENTS

(71) Applicant: Howmedica Osteonics Corp., Mahwah, NJ (US)

(72) Inventors: Damon J. Servidio, Towaco, NJ (US); Anthony K. Hedley, Phoenix, AZ (US)

(73) Assignee: Howmedica Osteonics Corp., Mahwah, NJ (US)

(*) Notice: Subject to any disclaimer, the term of this patent is extended or adjusted under 35 U.S.C. 154(b) by 79 days.

(21) Appl. No.: 17/352,496

(22) Filed: Jun. 21, 2021

(65) Prior Publication Data

US 2021/0307916 A1    Oct. 7, 2021

Related U.S. Application Data

(62) Division of application No. 16/419,232, filed on May 22, 2019, now Pat. No. 11,065,124.

(Continued)

(51) Int. Cl.
*A61F 2/38*    (2006.01)
*A61F 2/30*    (2006.01)

(52) U.S. Cl.
CPC ............ *A61F 2/3859* (2013.01); *A61F 2/389* (2013.01); *A61F 2/3836* (2013.01);
(Continued)

(58) Field of Classification Search
CPC .............. A61F 2/3859; A61F 2/30734; A61F 2002/30736
See application file for complete search history.

(56) References Cited

U.S. PATENT DOCUMENTS 4,731,086 A    3/1988    Whiteside et al.
4,936,847 A    6/1990    Manginelli
(Continued)

FOREIGN PATENT DOCUMENTS

CA    2841170 A1    1/2013
DE    3930033 A1    3/1990
(Continued)

OTHER PUBLICATIONS

Custom Impants Brochure, Ossis , 2013.
European Search Report including the Written Opinion from Application No. EP 19175880 dated Sep. 11, 2019, 5 pages.

*Primary Examiner* — Javier G Blanco
(74) *Attorney, Agent, or Firm* — Lerner David LLP

(57) ABSTRACT

A femoral assembly includes a femoral component that includes condylar portions and an anterior flange portion. The condylar portions and anterior flange portion together define an outer side of the femoral component for articulating with a tibial prosthesis and an inner bone facing side opposite the outer side. The inner bone facing side defines five intersecting component inner surfaces that each extend from a lateral side of the femoral component to a medial side thereof. A femoral augment includes condylar portions and an anterior flange portion. The condylar portions and anterior flange portion together define an outer side of the femoral augment comprised of five intersecting augment outer surfaces and an inner side comprising no more than three intersecting augment inner surfaces. The augment outer surfaces correspond to the component inner surfaces of the femoral component. The augment inner surfaces correspond to resected surfaces of a distal femur.

20 Claims, 5 Drawing Sheets

Related U.S. Application Data

(60) Provisional application No. 62/676,329, filed on May 25, 2018.

(52) U.S. Cl.
CPC . *A61F 2/30734* (2013.01); *A61F 2002/30011* (2013.01); *A61F 2002/30616* (2013.01); *A61F 2002/30621* (2013.01); *A61F 2002/30736* (2013.01); *A61F 2002/3863* (2013.01)

(56) References Cited

U.S. PATENT DOCUMENTS

| | | |
|---|---|---|
| 4,950,298 A | 8/1990 | Gustilo et al. |
| 5,035,714 A | 7/1991 | Willert et al. |
| 5,080,674 A | 1/1992 | Jacobs et al. |
| 5,226,915 A | 7/1993 | Bertin |
| 5,370,693 A | 12/1994 | Kelman et al. |
| 5,387,241 A | 2/1995 | Hayes |
| 5,458,637 A | 10/1995 | Hayes |
| 5,549,685 A | 8/1996 | Hayes |
| 5,571,194 A | 11/1996 | Gabriel |
| 5,609,645 A | 3/1997 | Vinciguerra |
| 5,702,460 A | 12/1997 | Carls et al. |
| 5,755,800 A | 5/1998 | O'Neil et al. |
| 5,766,255 A | 6/1998 | Slamin et al. |
| 5,879,393 A | 3/1999 | Whiteside et al. |
| 5,984,969 A | 11/1999 | Matthews et al. |
| 6,005,018 A | 12/1999 | Cicierega et al. |
| 6,074,424 A | 6/2000 | Perrone, Jr. et al. |
| 6,896,702 B2 | 5/2005 | Collazo |
| 7,175,665 B2 | 2/2007 | German et al. |
| 7,357,817 B2 | 4/2008 | D'Alessio, II |
| 7,537,664 B2 | 5/2009 | O'Neill et al. |
| 7,547,327 B2 | 6/2009 | Collazo |
| 7,837,737 B2 | 11/2010 | Hedley et al. |
| 8,187,280 B2 | 5/2012 | May et al. |
| 8,268,007 B2 | 9/2012 | Barsoum et al. |
| 8,292,967 B2 | 10/2012 | Brown et al. |
| 8,632,599 B1 | 1/2014 | Bonitati et al. |
| 8,715,357 B2 | 5/2014 | Samuelson et al. |
| 8,728,387 B2 | 5/2014 | Jones et al. |
| 9,162,008 B2 | 10/2015 | Serafin, Jr. et al. |
| 9,180,010 B2 | 11/2015 | Dong et al. |
| 9,320,603 B2 | 4/2016 | Lieberman et al. |
| 9,408,699 B2 | 8/2016 | Stalcup et al. |
| 9,456,901 B2 | 10/2016 | Jones et al. |
| 9,532,879 B2 | 1/2017 | Lieberman et al. |
| 9,668,880 B2 | 6/2017 | Samuelson et al. |
| 2002/0111692 A1 | 8/2002 | Ralph et al. |
| 2011/0015751 A1 | 1/2011 | Laird |
| 2012/0158152 A1 | 6/2012 | Claypool et al. |
| 2012/0185053 A1 | 7/2012 | Berger |
| 2012/0209391 A1 | 8/2012 | Cipolletti et al. |
| 2013/0013077 A1 | 1/2013 | Metzger et al. |
| 2014/0005791 A1 | 1/2014 | Bonitati et al. |
| 2014/0081408 A1 | 3/2014 | Lieberman et al. |
| 2014/0081410 A1 | 3/2014 | Lieberman et al. |
| 2014/0277528 A1 | 9/2014 | Mines et al. |
| 2015/0335438 A1 | 11/2015 | Pierce et al. |
| 2016/0367372 A1 | 12/2016 | Samuelson et al. |
| 2017/0027707 A1 | 2/2017 | Cremascoli |
| 2017/0100132 A1 | 4/2017 | Collazo |

FOREIGN PATENT DOCUMENTS

| | | |
|---|---|---|
| EP | 1360950 A2 | 11/2003 |
| FR | 2729560 A1 | 7/1996 |
| JP | 2014239900 A | 12/2014 |
| WO | 2009089581 A1 | 7/2009 |
| WO | 2013134333 A1 | 9/2013 |

VARIABLE THICKNESS FEMORAL AUGMENTS

CROSS-REFERENCE TO RELATED APPLICATIONS

This application is a divisional of U.S. application Ser. No. 16/419,232, filed May 22, 2019, which claims the benefit of the filing date of U.S. Provisional Patent Application No. 62/676,329, filed May 25, 2018, the disclosures of which are hereby incorporated herein by reference in their entirety.

BACKGROUND OF THE INVENTION

Total knee arthroplasty ("TKA") is a common orthopedic procedure for knee joints. Prior to implanting prosthetic components in a knee joint of a patient, a surgeon generally resects at least a portion of the patient's native bone in order to create surfaces and/or recesses for accepting or receiving at least a portion of the prosthetic components being implanted. Generally, a surgeon only resects the amount of bone that is needed in order to properly implant the prosthetic components in the joint because once native bone is resected from a joint, it is gone forever. This is typically done using cutting jigs to perform multiple resections of a distal femur and a proximal tibia.

When previously implanted prosthetic components fail for any one of a variety of reasons, a revision procedure is often necessary. An issue generally encountered by surgeons replacing joints during a revision procedure is the additional loss of native bone near the joint being replaced. This bone loss is typically due to movement of the component or components after implantation or even degeneration of the bone. In addition, because prosthetic components are typically cemented to bone or utilize porous surfaces that promote bone growth into the prosthesis, revision procedures often involve the removal of bone at the prosthesis interface when the prosthesis is removed. In this regard, the remaining bone may not be suitable for connection to a revision prosthesis and may, therefore, need to be resurfaced which requires further removal of bone.

The bone loss may be so extensive that implanting a revision prosthesis onto the bone without augmentation would result in an undesirable shift of the patient's joint line, instability of the joint, and/or improper connection between the prosthesis and bone. In this regard, augments are commonly placed between the patient's bone and the prosthesis to help compensate for the lost bone. This generally includes filling gaps where there is missing bone with bone cement and/or applying multiple shim-like augments at different locations between the bone and prosthesis where augmentation is needed. This often results in a tedious trialing process and typically requires re-cutting the bone while assessing knee balance in flexion and extension thereby significantly extending the time of the operation. Therefore, further improvements are desirable.

BRIEF SUMMARY OF THE INVENTION

Disclosed herein are assemblies, devices, kits, and methods for augmenting a distal femur in a revision procedure to compensate for bone loss. In particular, a femoral assembly is described which includes a femoral component and a femoral augment. The femoral component and augment can be trial prostheses or final, implantable prostheses. The augment is configured to connect to an inner or bone facing side of the femoral component. In this regard, the femoral augment includes condylar portions and an anterior flange portion which are configured to seat on corresponding condylar portions and anterior flange portion of the femoral component. The femoral component has standard five intersecting planar bone facing surfaces. The femoral augment includes corresponding five intersecting planar implant facing surfaces. The augment also includes three intersecting planar bone facing surfaces which are intended to be mounted onto corresponding resected surfaces of a distal femur.

Also described is a kit in which multiple femoral augments, both trial augments and prosthesis augments, are provided in the kit in a one-to-one relationship. More particularly, the kit includes sets of different sized augments such that multiple augments of a first size, a second size, a third size, and so on are provided. Each set of augments that is of the same nominal size has dimensions that are consistent amongst each augment in the set and also has dimensions that differ amongst each augment in the set. More particularly, augments that are of the same nominal size have inner bone facing surfaces that intersect each other at the same relative angles and bone facing surfaces of the same lengths so that a resected distal femur can be separately mounted with each augment in the set of same size augments without having to re-cut the distal femur. However, each augment within the set of same size augments has a differing thickness at a distal end of the augment so that a flexion gap of a knee joint can be varied simply by switching out one augment for another of the same nominal size but with a different thickness. This greatly simplifies the trialing process as it allows for flexion and extension gaps to be balanced without having to re-cut the femur.

Further described is a method in which a previously implanted femoral component is removed from the distal femur. The distal femur is measured so that a nominal size implant and augment are selected based on such measurement. The distal femur is resected using a cutting guide that corresponds to the selected size augment and femoral component. Multiple trial augments of the same nominal size but with different thicknesses may be mounted to the resected femur so as to assess flexion and extension gap balance. Thereafter, a corresponding final prosthetic augment and femoral component are mounted to the femur based on the flexion and extension gap assessment using the augment trials.

In one aspect of the present disclosure, a femoral assembly for a total knee prosthesis includes a femoral component having condylar portions and an anterior flange portion. The condylar portions and anterior flange portion together define an outer side of the femoral component for articulating with a tibial prosthesis and an inner bone facing side opposite the outer side. The inner bone facing side defines five intersecting component inner surfaces that each extend from a lateral side of the femoral component to a medial side thereof. The assembly also includes a femoral augment having condylar portions and an anterior flange portion. The condylar portions and anterior flange portion of the femoral augment together define an outer side of the femoral augment comprised of five intersecting augment outer surfaces and an inner side comprising no more than three intersecting augment inner surfaces. The augment outer surfaces correspond to the component inner surfaces of the femoral component. The augment inner surfaces correspond to resected surfaces of a distal femur.

Additionally, the femoral component includes an intercondylar portion that may comprise a cam box extending from the inner bone facing side of the femoral component such that at least some of the component inner surfaces are interrupted by the cam box. The femoral component may include a stem boss extending from the cam box. The femoral augment may include a strut extending between the condylar portions thereof such that the strut, anterior flange and condylar portions of the femoral augment define an opening configured to receive the cam box. The femoral component may include a posterior recess configured to receive the strut and an anterior recess configured to receive at least a portion of the anterior flange of the femoral augment. The posterior and anterior recesses may intersect the cam box and may extend in a lateral-medial direction.

Continuing with this aspect, the femoral component may include depressions on the inner bone facing side such that spaces are formed between the femoral component and femoral augment when the augment outer surfaces are seated on the corresponding component inner surfaces. Also, the femoral augment may include a plurality of porous patches on the inner side and outer side thereof.

In another aspect of the present disclosure, a kit for augmenting a resected femur in a revision total knee arthroplasty includes a first set of femoral augments each having condylar portions and a flange portion connecting the condylar portions. The condylar portions and flange portion define outer and inner sides of the respective femoral augment. The outer side and inner side each have a plurality of intersecting planar surfaces wherein the intersecting planar surfaces of the outer side includes anterior, posterior, and distal surfaces, and the inner side includes anterior, posterior, and distal surfaces. An anterior thickness of each of the femoral augments in the first set of femoral augments is defined between the anterior surfaces of the outer and inner sides, a posterior thickness of each of the femoral augments is defined between the posterior surfaces of the outer and inner sides, and a distal thickness is defined between the distal surfaces of the outer and inner sides. The distal thickness is different between each femoral augment in the first set and the anterior and posterior thicknesses are constant.

Additionally, the distal thickness may vary in increments of 1 to 3 mm. The distal surface of the inner side of each of the femoral augments in the first set of femoral augments may have a length defined between the anterior and posterior surfaces of the inner side and such distal surface length is constant amongst each of the femoral augments in the first set.

The kit may further include a second set of femoral augments each having condylar portions and a flange portion defining outer and inner sides thereof. The inner side of each of the augments of the second set of augments may include a distal surface intersected by posterior and anterior surfaces such that a length of the distal surface of each of the second set of augments is defined between the posterior and anterior surfaces thereof and such that the length of the distal surface of each of the second set of augments differs from the distal surface length of the first set of augments but is constant amongst each augment within the second set of augments. A distal thickness of each of the augments of the second set of augments may be defined between the distal surface of the inner side thereof and an distal surface of the outer side thereof such that the distal thickness of each of the second set of augments differs from augment to augment thereof. A first angle defined between the anterior and distal surfaces of the inner side of the first set of femoral augments may be constant amongst all femoral augments in the first set and may differ from that of the second set of femoral augments.

The kit may further include a plurality of femoral components including a first femoral component having a component inner side configured to interface with the outer side of the first set of femoral augments, and a second femoral component having a component inner side configured to interface with the outer side of the second set of femoral augments. Even further, the kit may include a plurality of cutting guides including a first cutting guide associated with the first set of femoral augments, and a second cutting guide associated with the second set of femoral augments.

Continuing with this aspect, each femoral augment in the first set may include a strut extending between the condylar portions such that the strut, anterior flange, and condylar portions of each of the femoral augments define an opening configured to receive a cam box of a corresponding femoral component. The inner side of each of the femoral augments of the first set of femoral augments may include no more than the anterior, posterior, and distal surfaces thereof, and the outer side of each of the femoral augments of the first set of augments may include a posterior chamfer surface interposed between the distal surface and posterior surface thereof and an anterior chamfer surface interposed between the distal surface and anterior surface thereof. Each of the femoral augments of the first set of femoral augments may include a plurality of porous patches on the inner side and outer side thereof. The porous patches disposed at the outer side of each of the femoral augments of the first set of femoral augments may be recessed within a solid metallic frame thereof. The solid metallic frame may have an H-shaped cross-sectional profile.

In an even further aspect of the present disclosure, a femoral assembly for a total knee prosthesis includes a femoral component having a first side for articulating with a tibial prosthesis and a second side opposite the first side. The second side includes five component inner surfaces. The assembly also includes a femoral augment having a third side including five augment outer surfaces and a fourth side including no more than three augment inner surfaces. The augment outer surfaces correspond to the component inner surfaces, and the augment inner surfaces correspond to resected surfaces of a distal femur.

Additionally, the femoral component may include condylar portions and an anterior flange portion, and the five component inner surfaces may extend along the condylar portions and anterior flange portion. The femoral augment may include condylar portions and an anterior flange portion and the five augment inner surfaces may extend along the condylar portions and anterior flange portion so that the femoral augment can conformingly seat on the femoral component. The component inner surfaces may each intersect an adjacent component inner surface and extend in a lateral-medial direction from a lateral side of the femoral component to a medial side of the femoral component. The augment outer surfaces may each intersect an adjacent augment outer surface and extend in a lateral-medial direction from a lateral side of the femoral augment to a medial side of the femoral augment.

In yet another aspect of the present disclosure, method of augmenting a femur in a revision total knee arthroplasty includes a.) removing a previously implanted prosthesis from a femur; b.) measuring a distal end of the femur to determine a nominal size augment and corresponding femoral component for connection to the distal end of the femur; c.) resecting the distal femur along a plurality of planes to form a plurality of resected surfaces; d.) selecting an augment from a set of augments each being of the same determined nominal size wherein each augment of the set of augments has a plurality of inner surfaces and outer surfaces and wherein a thickness between some of the inner surfaces and outer surfaces is constant between each of the augments of the set of augments and a thickness between other inner surfaces and outer surfaces differs between each of the augments of the set of augments; e.) connecting the selected augment to the resected surfaces of the distal femur; f.) assessing the flexion and extension gap; and g.) selecting another femoral augment from the set of augments if it is determined that the extension gap is too loose or too tight and repeating steps d-f until the flexion gap is satisfactory.

BRIEF DESCRIPTION OF THE DRAWINGS

The features, aspects, and advantages of the present invention will become better understood with regard to the following description, appended claims, and accompanying drawings in which:

DETAILED DESCRIPTION

When referring to specific directions in the following discussion of certain implantable devices, it should be understood that such directions are described with regard to the implantable device's orientation and position during exemplary application to the human body. Thus, as used herein, the term "proximal" means close to the heart and the term "distal" means more distant from the heart. The term "anterior" means toward the front of the body or the face and the term "posterior" means toward the back of the body. The term "medial" means toward the midline of the body and the term "lateral" means away from the midline of the body. Also, as used herein, the terms "about," "generally" and "substantially" are intended to mean that slight deviations from absolute are included within the scope of the term so modified.

Figure 1:
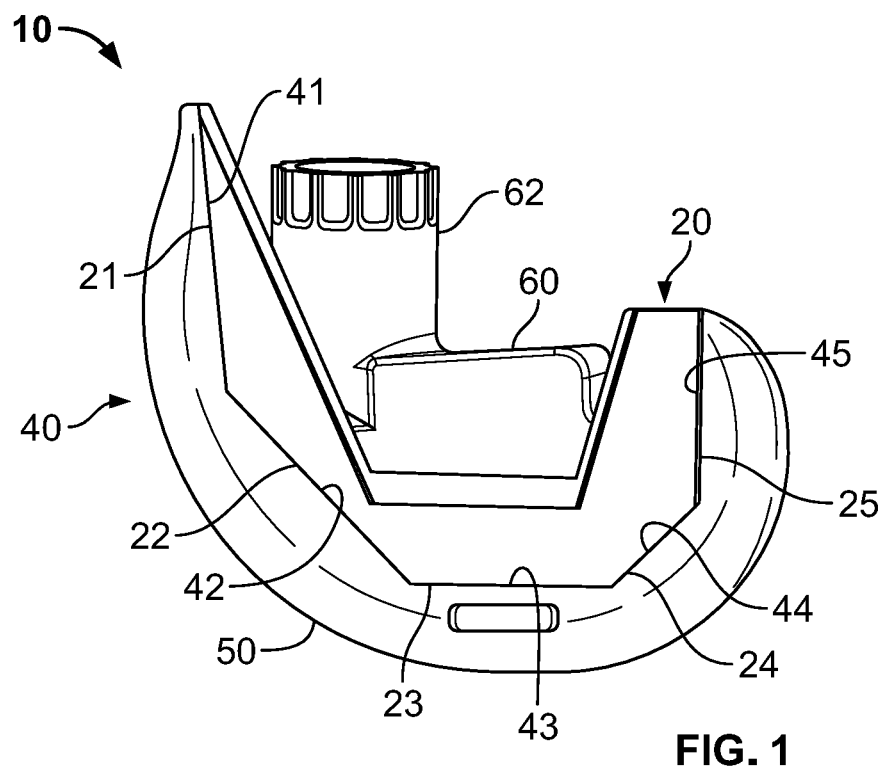
FIG. 1 is a side elevational view of a femoral component and augment according to an embodiment of the present disclosure.
Figure 2:
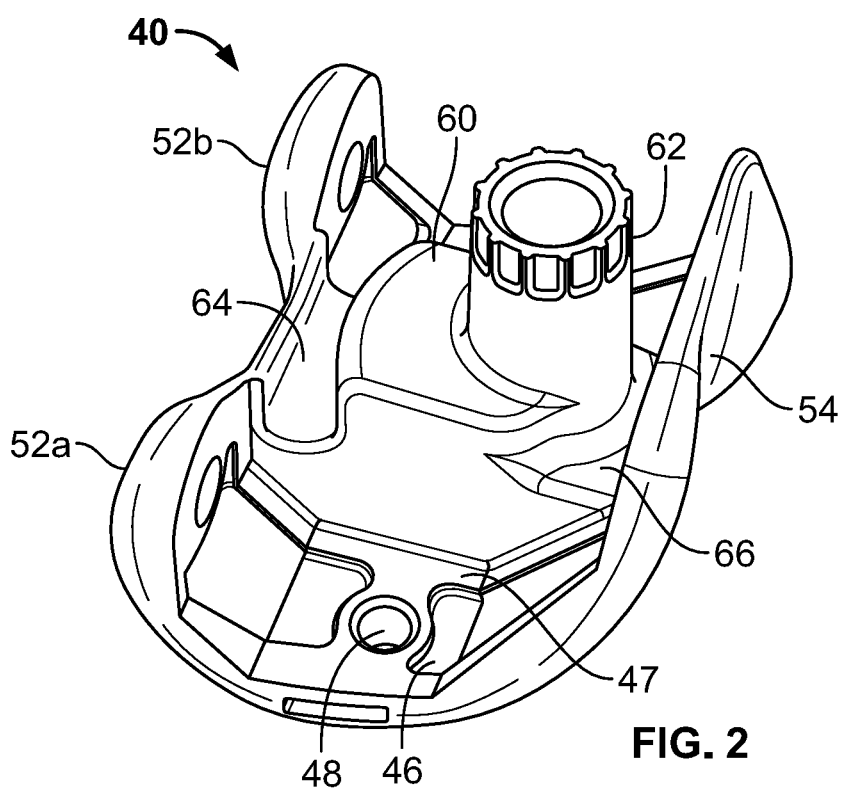
FIG. 2 is a top perspective view of the femoral component of FIG. 1.

FIG. 1 depicts a femoral assembly 10 that includes a femoral component 40 and a femoral augment 20 coupled to the femoral component 40. Femoral component 40, as shown in FIG. 2, is a five-cut, revision femoral component and, as depicted, may be a trial implant or a final implant. Five-cut femoral components are common in the field of TKA as it is standard practice to resect a distal femur with five planar cuts using a series of cutting jigs. Thus, most current TKA femoral components are configured with corresponding surfaces. Femoral component 40 is no exception and has a bone facing side disposed opposite an outer articular surface 50 that has five intersecting planar surfaces, namely first component inner surface or anterior surface 41, second component inner surface or anterior chamfer surface 42, third component inner surface or distal surface 43, fourth component inner surface or posterior chamfer surface 44, and fifth component inner surface or posterior surface 45. Component 40 also includes medial and lateral condylar portions 52a-b connected by an anterior flange 54 and an intercondylar portion.

Femoral component 40 also includes a cam box 60 that that extends from the bone facing side thereby interrupting the component inner surfaces, and a stem boss for receiving an intramedullary stem. Cam box 60 includes a camming surface (not shown) for articulation with a post of a tibial component, as is known in the art. In this regard, femoral component 40 is configured to connect directly to a distal femur that has been resurfaced in the usual way with five intersecting planar resections.

However, femoral component 40 is also configured to mate with femoral augment 20. In this regard, femoral component 40 includes posterior and anterior recesses 64, 66 that intersect cam box 60 and extend in a lateral-medial direction. Such recesses 64, 66 respectively receive an anterior flange 27 and strut 29 of augment 20, as described below. In addition, femoral component 40 includes depressions 46 that extend along the bone facing side of the femoral component 40, which form a raised rim 47 that defines a perimeter of depressions 46. As is discussed further below, augment 40 seats on rim 47 while depressions 46 forms gaps therebetween for cement/adhesive for connection between the femoral component 40 and augment 20. Femoral component 40 also includes threaded openings 48 extending into the bone facing side thereof at both the medial and lateral condylar portions 52a-b. Such threaded openings 48 facilitate threaded connection between augment 20 and femoral component 40 to further solidify fixation of the two components.

Augment 20, as depicted in FIGS. 3A-3D, generally includes medial and lateral condylar portions 26a-b, an anterior flange 27, and a bridge member or strut 29. Medial and lateral condylar portions 26a-b are connected via anterior flange 27 and strut 29 so that condylar portions 26a-b, flange 27, and strut 29 together define an augment opening 30 that is configured to receive stem boss 62 and cam box 60 of femoral component 40. In this regard, condylar portions 26a-b are configured to seat on corresponding condylar portions 52a-b of femoral component 40, strut 29 is configured to correspondingly seat within posterior recess 64, and anterior flange 27 is configured to seat on anterior flange 54 of femoral component 40 while also seating at least partially within anterior recess 66.

Condylar portions 26a-b and anterior flange 27 together define five planar intersecting surfaces 21, 22, 23, 24, 25 on an implant/component facing side of augment 20, which correspond to surfaces 41, 42, 43, 44, 45 of femoral component 40. Thus, augment 20 includes first augment outer surface or anterior surface 21, second augment outer surface or anterior chamfer surface 22, third augment outer surface or distal surface 23, fourth augment outer surface or posterior chamfer surface 24, and fifth augment outer surface or posterior surface 25.

Condylar portions 26a-b and anterior flange 27 also define three planar intersecting surfaces 31, 32, 33 on a bone facing side thereof. Such surfaces 31, 32, 33 include a first augment inner surface or anterior surface 31, a second augment inner surface or distal surface 32, and a third augment inner surface or posterior surface 33. While the bone facing side of augment 20 may include more than three planar intersecting surfaces, such as four or five, for example, it is preferable that augment 20 include three inner surfaces to correspond to three resected surfaces of a femur. This allows a thickness of augment 20 to be varied in a way that no portion of augment 20 is too thin, as could be the case if augment 20 had five inner bone facing surfaces. The three inner surfaces 31, 32, and 33 also allows for simplified resection of a femur while also allowing augment 20 to be connected to a femoral component, such as component 40, with the standard five planar surfaces, as described above. Thus, augment 20 can adapt a three-cut femur to a standard five-cut prosthesis, which may have the added benefit of saving additional bone during a revision procedure.

Figure 3A:
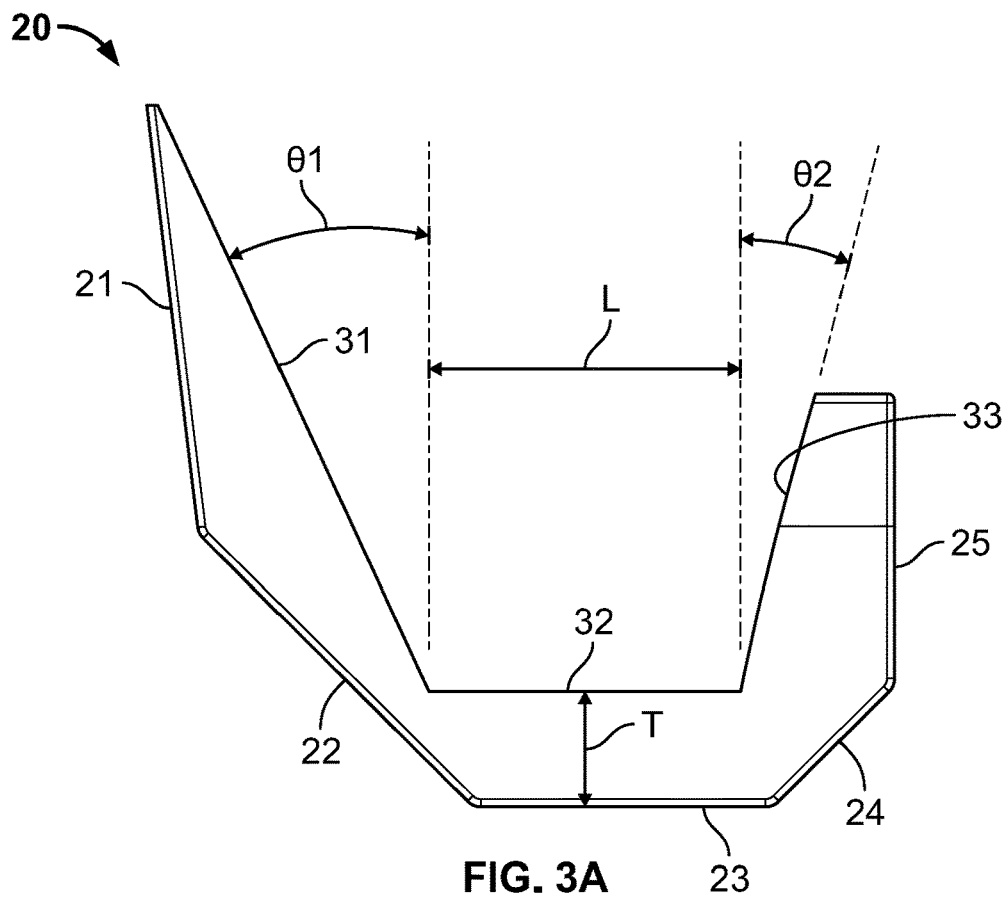
FIG. 3A is side elevational view of the augment of FIG. 1.
Figure 3B:
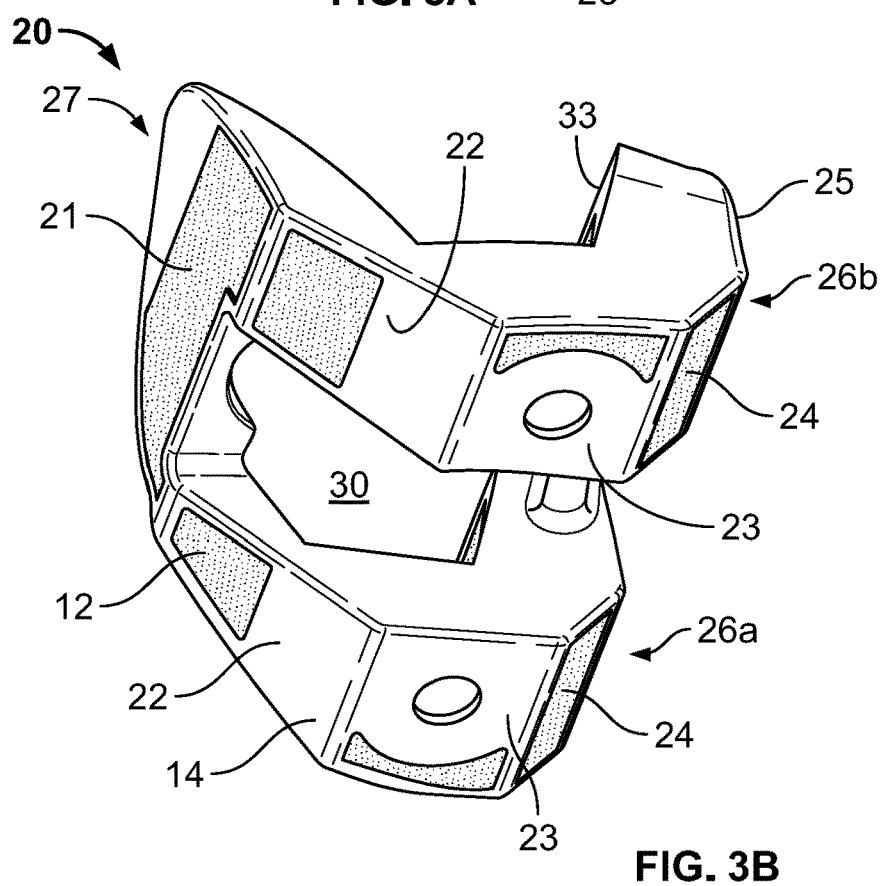
FIG. 3B is a bottom perspective view of the augment of FIG. 1.
Figure 3C:
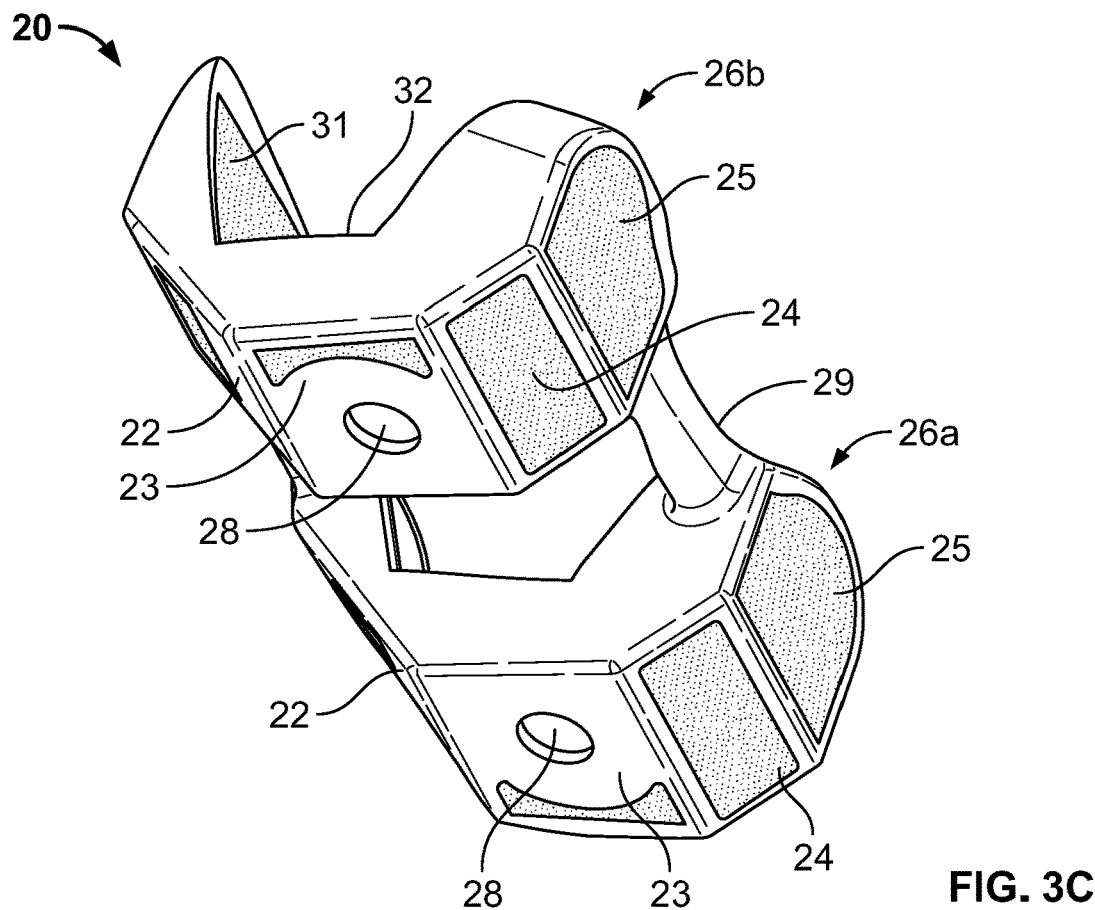
FIG. 3C is another bottom perspective view of the augment of FIG. 1.

As best shown in FIG. 3A, first augment inner surface 31 intersects second augment inner surface 32 at a first absolute angle $\theta 1+90$ degrees, while third augment inner surface 33 intersects second augment inner surface 32 at a second absolute angle $\theta 2+90$ degrees. $\theta 1$ can be any angle within a range of 1 to 30 degrees, while $\theta 2$ can be any angle within a range of 1 to 50 degrees. However, in one particular example, $\theta 1$ is 25 degrees, and $\theta 2$ is 15 degrees. Such angles $\theta 1$ and $\theta 2$ are relative to a vertical axis that is perpendicular to distal surface 32 and each correspond to a respective resection angle of a femur that receives augment 20. In addition, second augment inner surface 32 spans a length "L" in an anteroposterior direction between first and second augment inner surfaces 31, 33. Such length L corresponds to a nominal size of augment 20 such that, for example, a first length L1 corresponds to a size 1 augment, a second length L2 corresponds to a size 2 augment, a third length L3 corresponds to a size 3 augment, and so on.

Figure 3D:
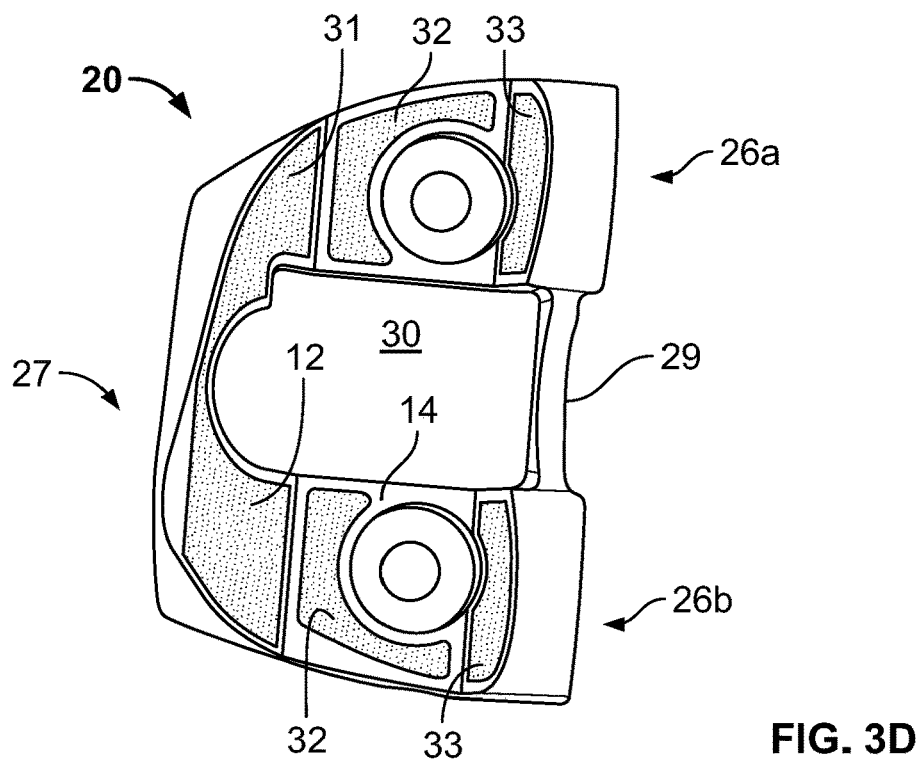
FIG. 3D is a top perspective view of the augment of FIG. 1.
Figure 5A:
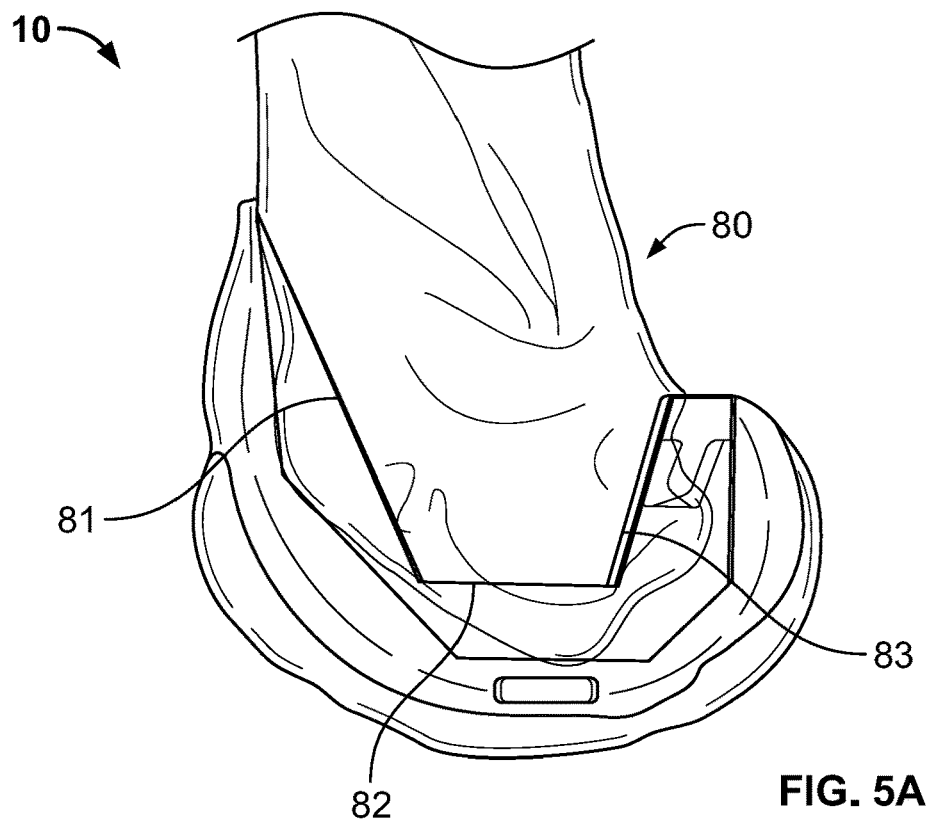
FIG. 5A is the femoral component and augment of FIG. 1 overlaying a distal femur to illustrate a connection thereto.
Figure 5B:
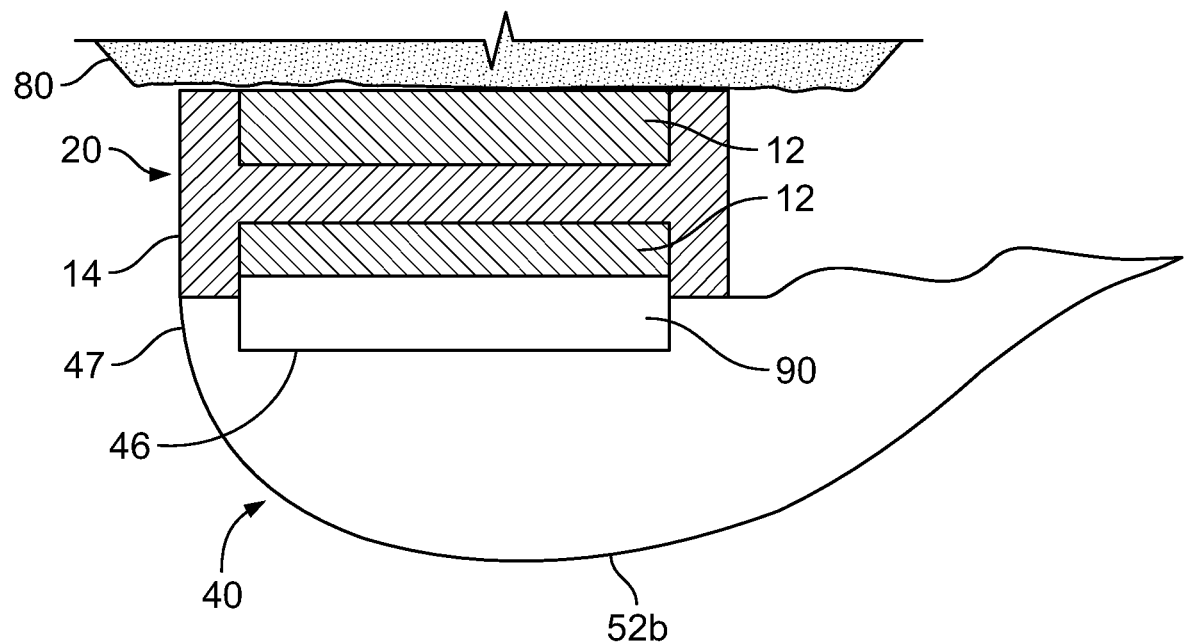
FIG. 5B is a schematic, partial cross-sectional view of an interface between a resected femur and the femoral component and augment of FIG. 1.

Augment 20, as well as femoral component 40, is constructed from biocompatible material, such as titanium, stainless steel, cobalt-chromium, and the like. In addition, augment 20 includes porous patches 12 on both the bone facing and component facing sides thereof. Such patches 12 can each have a thickness of about 1 mm, for example, and are preferably included on each surface of augment 20 such that they are surrounded by solid, nonporous metallic material which acts as a structural frame 14 for strength of the augment. Porous patches 12 on the bone facing side may be flush with the surrounding solid material 14 so that when augment 20 is mounted to a resected femur, porous patches 12 directly contact the bone for bone ingrowth into the porous structure of patches 12. Alternatively, patches 12 on the bone facing side may be recessed within the surrounding solid structure 14 so as to provide space for bone cement. Such cement may fill the porous structure for enhanced fixation. Similarly, porous patches 12 on the component facing side of augment 20 may be recessed so that when femoral component 40 and augment 20 are connected, depressions 46 within femoral component 40 and recessed patches 12 of augment 20 form spaces that allow for a cement mantle to be formed between augment 20 and femoral component 40 as best shown in FIG. 5B and as described in more detail below. Porous patches 12 on the component facing side helps promote cemented fixation. Augment 20 also includes screw openings 28 extending through distal surfaces 23, 32 of condylar portions 26a-b to allow augment 20 to be threadedly fixed via fasteners to femoral component 40. As best shown in FIG. 3D, such holes 28 are countersunk on the bone facing side so that fasteners extending through openings 28 do not sit proud of distal surface 32 so as to not interfere with direct contact of distal surface 32 with bone.

Augment 20, including porous patches 12 thereof, may be a monolithic/unitary structure that is formed layer-by-layer using an additive layer manufacturing (ALM), i.e., 3D printing, process so no separate connection mechanism is necessary to bring together any of the components of augment 20 (e.g., solid and porous structures). In some examples, ALM processes are powder-bed based and involve one or more of selective laser sintering (SLS), selective laser melting (SLM), and electron beam melting (EBM), as disclosed in U.S. Pat. Nos. 7,537,664; 8,728,387; 9,180,010; and 9,456,901, the disclosures of which are hereby incorporated by reference in their entireties herein. In this regard, it is contemplated that augment 20 may have other configurations that can also be manufactured via ALM. In one such embodiment, instead of having porous patches 12 positioned on opposite sides of augment 20 and separated by a solid layer 14 of augment 20, porous patches 12 may extend entirely through solid structure 14. This helps provide additional thickness to each porous patch 12 so as to facilitate bone growth therein.

Augment 20, as depicted, is intended for final implantation and is preferably provided in a kit with other similar prosthetic augments. Moreover, trial augments that are visually identical to augment 20 absent porous patches 12 are also provided in the kit to correspond one-to-one with the final prosthetic augments of the kit. Thus, discussion below regarding augments applies equally to trial augments and final prosthetic augments. The kit, as described herein, along with the particular configuration of the augments within the kit greatly simplifies trialing and implantation. More particularly, each kit includes a plurality of augments 20 that are of different nominal size, such as size 1, size 2, size 3, size 4 augments and so on. Such nominal sizes correspond to the nominal size of a corresponding femoral component 40. In addition, such sizes, among other things, are a function of the length L of distal surface 32 such that length L increases with each increase in nominal size, as mentioned above.

In addition to having multiple augments 20 of differing nominal size, the kit includes sets of augments 20 of the same nominal size where each augment 20 within a set has a different thickness. Augment thickness is defined between the bone contacting side and component facing side of each augment 20, as illustrated by the thickness "T" in FIG. 3A. However, the thickness of the augments 20 in a set of same nominal size augments only differs in certain locations and not others. In other words, the thickness of each augment 20 in the kit that are of the same nominal size is constant at certain locations while different at other locations. This is exemplified in FIG. 4 which shows a first augment 20 overlaying a second femoral augment 20' of the same nominal size. As can be seen, the thickness of first augment 20 between first inner surface 31 and first outer surface 21 as well as for third inner surface 33 and fifth outer surface 25 is that same as the thickness of second augment 20' between first inner surface 31' and first outer surface 21' as well as for third inner surface 33' and fifth outer surface 25'. However, the thickness of second augment 20' between first, second, and third inner surfaces 31', 32', 33' and second, third and fourth outer surfaces 22', 23', 24' is greater than that of first augment 20. Thus, it could be generally said that second augment 20' has a greater distal thickness than first augment 20 while having the same anterior and posterior thickness as first augment 20. This is true amongst all augments in the kit that are of the same nominal size. Thus, the kit may have a set of size 4 augments 20 that include a first size 4 augment, a second size 4 augment, and a third size 4 augment where the first, second, and third size 4 augments have differing distal thicknesses and constant anterior and posterior thicknesses. Such thickness differences may be in increments of 1 to 3 mm. Thus, for example, the thickness between distal inner surface 32 and distal outer surface 23 of first, second, and third size 4 augments may be 10 mm, 13 mm, and 16 mm respectively. F component 40 may have an additional thickness of about 3 mm. Thus, the femoral augments may be designated as being 13 mm, 16 mm, and 19 mm augments, respectively, as such designation takes into account the overall thickness of assembly 10. The same pattern may be repeated for each size within the kit, such as for size 1, size 2, and size 3 sets of augments, for example.

Figure 4:
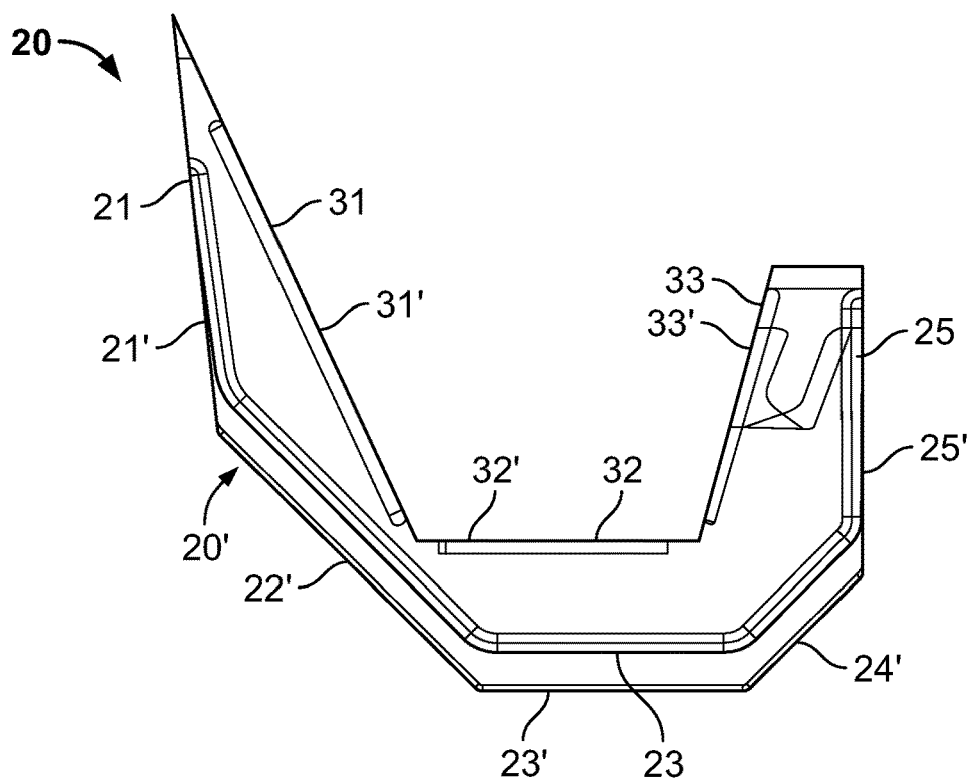
FIG. 4 is a side elevational view of the augment of FIG. 1 overlaying a second augment.

As suggested above, each augment 20 that is in a set of augments of the same nominal size has the same length L and same angles θ1 and θ2. For example, for a set of size 4 augments, each one of those size 4 augments have the same length L and the same angles θ1 and θ2, as is illustrated in FIG. 4. However, the length L and angles θ1 and θ2 differ between sizes such that these parameters are different between size 1, size 2, size 3, and size 4 augments, for example. Thus, to summarize, the kit includes multiple sets of different sized augments where each augment that is in a set of the same nominal size has the same length L, same angles θ1 and θ1, same anterior and posterior thicknesses, and a different distal thickness from that of other augments in the set. However, augments of different nominal size have different L and θ1 and θ2 dimensions. The below table is further illustrative.

|  | Size 1 | Size 2 | Size 3 | Size 4 |
| --- | --- | --- | --- | --- |
| θ1 | Angle (1-1) | Angle (1-2) | Angle (1-3) | Angle (1-4) |
| θ1 | Angle (2-1) | Angle (2-2) | Angle (2-3) | Angle (2-4) |
| L | L1 | L2 | L3 | L4 |
| Augment #1 distal thickness | 10 mm | 10 mm | 10 mm | 10 mm |
| Augment #2 distal thickness | 13 mm | 13 mm | 13 mm | 13 mm |
| Augment #3 distal thickness | 16 mm | 16 mm | 16 mm | 16 mm |

In some embodiments, the kit may also include a plurality of cutting guides or jigs where each cutting jig corresponds to a set of same sized augments 20. For example, a first cutting jig corresponds to all size 1 augments, a second cutting jig corresponds to all size 2 augments, a third cutting jig corresponds to all size 3 augments, and so on. An exemplary cutting jig may be the 2-in-1 cutting jig disclosed as resection block 130 in U.S. Pub. No. 2017/0100132, the disclosure of which is hereby incorporated by reference herein. In this regard, each cutting jig is configured to cut a femur at the appropriate angles and with the appropriate dimensions to be associated with the L, θ1, and θ2 dimensions of the corresponding augments.

The above described kit of augments 20 provides for a simplified trialing process that reduces operating time. In this regard, once a femoral component 40 and augment 20 size are selected, distal femoral resections are made only once using the appropriate jig(s) as each augment 20 that is of the same nominal size can use the same bone cuts during the trialing process.

The method of using augment 20 in a revision procedure further exemplifies this simplicity. In the method, an operator removes the previously implanted prosthesis and measures an anteroposterior dimension of the femur 80 to determine which size augment 20 and femoral component 40 to select. A cutting jig associated with the selected size may then be applied to femur 80 so as to cut posterior and anterior surfaces 81, 83 that intersect a distal resected surface 82 of femur 80. Femur 80 is then resected along three intersecting planes so that posterior and anterior resected surfaces 81, 83 correspond to the θ1 and θ2 angles of the selected size augment 20 and so that the distal resected surface 82 substantially corresponds to the length L of such augment 20.

Thereafter, one of the trial augments in the kit that is of the selected nominal size is connected to a trial femoral component 40 and coupled to the resected femur 80. For example, the operator may have measured for a size 4 augment 20 and corresponding size 4 femoral component 40. The operator then selects one of the size 4 augments 20 from the kit and couples it to the femoral component 40 and then to the end of femur 80, as illustrated in FIG. 5A. Femoral component 40 is then articulated with a trial tibial component (not shown) to assess the flexion and extension gaps. An exemplary tibial component is disclosed in U.S. Pat. No. 7,357,817, the disclosure of which is hereby incorporated by reference herein. The flexion gap should already be balanced based the sizing step. Thus, once the flexion gap is set, there should be no further adjustments to the posterior side of the augment or bone, i.e., there should be no further adjustments to resected surface 83 or the posterior side of augment 20. In this regard, each augment 20 that is of the same nominal size, such as each size 4 augment for example, does not have a varying posterior or anterior thickness. However, the extension gap may need further adjustment. Hence, the differing distal thicknesses of the augments 20 within a set of same size augments 20. Since each same sized augment has the same length L and angles θ1 and θ2, no further resections of femur 80 are necessary to balance the extension gap. If the extension gap is not balanced by the selection of the first trial augment 20, the operator then selects a second trial augment 20 of the same nominal size but with a different distal thickness than the first. For example, if the first selected size 4 trial augment 20 results in an extension gap that is too tight, a second size 4 trial augment 20 with a small distal thickness may be selected. If the flexion gap is too loose, then a second trial augment 20 with a larger distal thickness may be selected. Regardless of the selection of augment 20, the flexion gap should not be affected since the posterior and anterior thickness is the same for each augment 20 that is of the same nominal size.

Once it is determined that the flexion and extension gaps are properly balanced using the trial augments, the operator connects a corresponding final augment 20 to the final femoral component 40 for implantation. To do this, the operator may apply a layer of cement between the augment 20 and final prosthesis 40 and then may insert fasteners into openings 28 and 48 to connect the two together. Thereafter, assembly 10 is mounted to femur 80 so that augment 20, including its porous patches 12, directly contacts resected surfaces of bone 80. However, in some embodiments, operator may apply a layer of cement between augment 20 and bone first.

FIG. 5B is a cross-section view depicting assembly 10 as mounted to resected distal femur 80. As shown, augment 20 has an H-shaped frame 14 of solid metallic material with porous patches 12 disposed within this frame 14. A porous patch 12 on the bone facing side of augment 20 directly contacts the resected distal femur 80 so that bone can grow into the porous structure of patch 12 for permanent fixation. At the opposite side of augment 20, augment 20 is cemented to femoral component 40 such that cement 90 is disposed in the space defined by the depression 46 of femoral component 40 and recess porous patch 12 of augment 20. Driving a screw through holes 28 and 48 to threadedly connect augment 20 to femoral component 40 increases the pressure of cement 90 between augment 20 and femoral component 40 which forces cement 90 deep within the porous structure of patch 12 thereby further solidifying the connection between augment 20 and component 40. Port holes (not shown) may be provided in augment to allow for pressure relief of the cement during assembly.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A femoral assembly for a total knee prosthesis, comprising:
a femoral component having condylar portions and an anterior flange portion, the condylar portions and anterior flange portion together define an outer side of the femoral component for articulating with a tibial prosthesis and an inner bone facing side opposite the outer side, the inner bone facing side defining five intersecting component inner surfaces that each extend from a lateral side of the femoral component to a medial side thereof; and
a femoral augment having condylar portions and an anterior flange portion, the condylar portions and anterior flange portion of the femoral augment together define an outer side of the femoral augment comprised of five intersecting augment outer surfaces and an inner side comprising no more than three intersecting augment inner surfaces, the augment outer surfaces corresponding to the component inner surfaces of the femoral component, the augment inner surfaces corresponding to resected surfaces of a distal femur.

2. The assembly of claim 1, wherein the femoral component includes an intercondylar portion that comprises a cam box extending from the inner bone facing side of the femoral component such that at least some of the component inner surfaces are interrupted by the cam box.

3. The assembly of claim 2, wherein the femoral component includes a stem boss extending from the cam box.

4. The assembly of claim 2, wherein the femoral augment includes a strut extending between the condylar portions thereof such that the strut, anterior flange and condylar portions of the femoral augment define an opening configured to receive the cam box.

5. The assembly of claim 4, wherein the femoral component includes a posterior recess configured to receive the strut and an anterior recess configured to receive at least a portion of the anterior flange of the femoral augment, the posterior and anterior recesses intersecting the cam box and extending in a lateral-medial direction.

6. The assembly of claim 1, wherein the femoral component includes depressions on the inner bone facing side such that spaces are formed between the femoral component and femoral augment when the augment outer surfaces are seated on the corresponding component inner surfaces.

7. The assembly of claim 6, wherein the femoral augment includes a plurality of porous patches on the inner side and outer side thereof.

8. A femoral assembly for a total knee prosthesis, comprising:
a femoral component having an outer articular side and an inner bone facing side opposite the articular side, the inner bone facing side defining five intersecting component surfaces comprising an anterior surface, a posterior surface, a distal surface, an anterior chamfer surface, and a posterior chamfer surface; and
a femoral augment having an outer side and an inner side opposite the outer side, the outer side comprising five intersecting augment outer surfaces which each respectively correspond to the five intersecting component surfaces, the inner side comprising no more than three intersecting augment inner surfaces.

9. The assembly of claim 8, wherein the femoral component includes a cam box extending from the inner bone facing side of the femoral component such that at least the distal surface is interrupted by the cam box.

10. The assembly of claim 9, wherein the femoral component includes a stem boss extending from the cam box.

11. The assembly as in one of claim 8, wherein the femoral component includes depressions on the inner bone facing side such that spaces are formed between the femoral component and femoral augment when the augment outer surfaces are seated on the corresponding component inner surfaces.

12. The assembly as in one of claim 8, wherein the femoral augment includes a plurality of porous patches on the inner side and outer side thereof.

13. A kit for augmenting a resected femur in a revision total knee arthroplasty, comprising:
a femoral component having an outer articular side and an inner bone facing side opposite the articular side, the inner bone facing side defining five intersecting component surfaces comprising an anterior surface, a posterior surface, a distal surface, an anterior chamfer surface, and a posterior chamfer surface;
a first femoral augment having an outer side and an inner side opposite the outer side, the outer side comprising five intersecting augment outer surfaces which each respectively correspond to the five intersecting component surfaces, the inner side comprising no more than three intersecting augment inner surface; and
a second femoral augment having an outer side and an inner side opposite the outer side, the outer side comprising five intersecting augment outer surfaces which each respectively correspond to the five intersecting component surfaces, the inner side comprising no more than three intersecting augment inner surface.

14. The kit of claim 13, wherein the femoral component includes a cam box extending from the inner bone facing side of the femoral component such that at least the distal surface is interrupted by the cam box.

15. The kit of claim 14, wherein the first and second femoral augments each include a first portion and a second portion spaced a distance from the first portion such that the augment is configured to receive the cam box between the first and second portions of the femoral augment.

16. The kit of claim 15, wherein the first and second femoral augments include a strut extending between and connecting the first and second portions.

17. The kit of claim 15, wherein the first and second portions each define a screw opening for receipt of a screw.

18. The kit of claim 17, wherein the outer and inner sides of each of the first and second femoral augments include a porous surface.

19. The kit of claim 18, wherein a first thickness between the outer and inner sides of the first femoral augment is equal to a corresponding first thickness between the outer and inner sides of the second femoral augment, and a second thickness between the outer and inner sides of the first femoral augment is different from a corresponding second thickness between the outer and inner sides of the second femoral augment.

20. The kit of claim 19, wherein the difference between the second thickness of the first femoral augment and the second thickness of the second femoral augment is 1 mm.

* * * * *